(12) United States Patent
Liverton et al.

(10) Patent No.: US 7,592,360 B2
(45) Date of Patent: Sep. 22, 2009

(54) 3-FLUORO-PIPERIDINES AS NMDA/NR2B ANTAGONISTS

(75) Inventors: Nigel J. Liverton, Harleysville, PA (US); Christopher F. Claiborne, Cambridge, MA (US); David A. Claremon, Maple Glen, PA (US); John A. McCauley, Maple Glen, PA (US)

(73) Assignee: Merck & Co., Inc., Rahway, NJ (US)

( * ) Notice: Subject to any disclaimer, the term of this patent is extended or adjusted under 35 U.S.C. 154(b) by 534 days.

(21) Appl. No.: 10/559,153

(22) PCT Filed: May 28, 2004

(86) PCT No.: PCT/US2004/017175

§ 371 (c)(1),
(2), (4) Date: Dec. 5, 2005

(87) PCT Pub. No.: WO2004/108705

PCT Pub. Date: Dec. 16, 2004

(65) Prior Publication Data

US 2007/0149568 A1 Jun. 28, 2007

Related U.S. Application Data

(60) Provisional application No. 60/475,938, filed on Jun. 4, 2003.

(51) Int. Cl.
*A01N 43/40* (2006.01)
*A01N 43/36* (2006.01)

(52) U.S. Cl. .................................... 514/317; 514/408
(58) Field of Classification Search ................ 514/317, 514/408
See application file for complete search history.

(56) References Cited

U.S. PATENT DOCUMENTS

| | | | |
|---|---|---|---|
| 3,184,462 | A | 5/1965 | Scarborough et al. |
| 3,933,832 | A | 1/1976 | Langbein et al. |
| 4,197,304 | A | 4/1980 | Sanczuk et al. |
| 6,300,333 | B1 | 10/2001 | Schaper et al. |

FOREIGN PATENT DOCUMENTS

| | | |
|---|---|---|
| DE | 4241632 | 6/1994 |
| EP | 532 456 | 12/1991 |
| FR | 2758327 | 1/1997 |
| FR | 2758328 | 1/1997 |
| WO | WO 94 21615 | 9/1994 |
| WO | WO 97 43279 | 11/1997 |
| WO | WO 97 45119 | 12/1997 |
| WO | WO 98 05336 | 2/1998 |
| WO | WO 98 31677 | 7/1998 |
| WO | WO 99 51589 | 3/1999 |
| WO | WO 02/68409 A1 * | 2/2002 |
| WO | WO 02/068409 | 9/2002 |

OTHER PUBLICATIONS

Lankin et al. Journal of American Chemical Society, 1993, 115, 3356-3357.*
Danysz, W., et al., Pharmacological Rev., vol. 50, pp. 597-664, 1998.
Dickenson, A., TIPS, vol. 11, pp. 307-309, 1990.
Wenzel, A., et al., Neurochemistry, vol. 7, pp. 45-48, 1995.
Kew, J. N. C., et al., Brit. J. Pharacology, vol. 123, pp. 463-472, 1998.
Boyce, S., et al., Neuropharmacology, vol. 38, pp. 611-623, 1999.
Laurie, D. J., et al., Mol. Brain Res., vol. 51, pp. 23-32, 1997.
Ishii, T., et al., J. Biol. Chem, vol. 268, pp. 2836-2843, 1993.
Max, M. B., et al., Clin. Neuropharmacology, vol. 18, pp. 360-368, 1995.
Knox, D. J., et al., Anaesth. Intens. Care, vol. 23, pp. 620-622, 1995.
Eide, P. K., et al., Pain, vol. 61, pp. 221-228, 1995.
Kristensen, J. D., et al., Pain, vol. 51, pp. 249-253, 1992.
Taniguchi, K, et al., Brit. J. Pharmacology, vol. 122, pp. 809-812, 1997.
Isabelle Parrot, et al., Synthesis of Substituted 3-Amino-6-Arylpyridazines via Suzuki Reaction, vol. 7, pp. 1163-1168, 1999.
J. Moragues, et al., Dopaminergic Activity in a Series of N-substituted 2-Aminopyrimides, vol. 35, pp. 951-964, 1980.

* cited by examiner

*Primary Examiner*—D. Margaret Seaman
*Assistant Examiner*—Nizal S Chandrakumar
(74) *Attorney, Agent, or Firm*—William Krovatin; John C. Todaro

(57) ABSTRACT

Compounds represented by Formula (I) or pharmaceutically acceptable salts thereof, are effective as NMDA NR2B antagonists useful for treating conditions such as, for example, Parkinson's disease, Alzheimer's disease, migraine, epilepsy and pain.

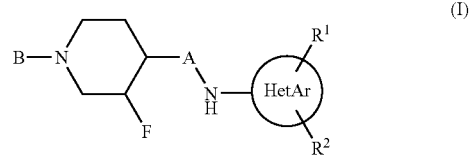

(I)

32 Claims, No Drawings

3-FLUORO-PIPERIDINES AS NMDA/NR2B ANTAGONISTS

Related Application Data

This is a National filing under 35 U.S.C. 371 of PCT/US2004/017175, filed May 28, 2004, which claims priority from U.S. Ser. No. 60/475,938, filed Jun. 4, 2003.

FIELD OF THE INVENTION

This invention relates to N-substituted nonarylheterocyclic compounds. In particular, this invention relates to N-substituted nonarylheterocyclic compounds that are NMDA NR2B antagonists useful for the treatment of Parkinson's disease and pain.

BACKGROUND OF THE INVENTION

Ions such as glutamate play a key role in processes related to chronic pain and pain-associated neurotoxicity—primarily by acting through N-methyl-D-aspartate ("NMDA") receptors. Thus, inhibition of such action—by employing ion channel antagonists, particularly NMDA antagonists—can be beneficial in the treatment and control of Parkinon's disease and pain.

NMDA receptors are heteromeric assemblies of subunits, of which two major subunit families designated NR1 and NR2 have been cloned. Without being bound by theory, it is generally believed that the various functional NMDA receptors in the mammalian central nervous system ("CNS") are only formed by combinations of NR1 and NR2 subunits, which respectively express glycine and glutamate recognition sites. The NR2 subunit family is in turn divided intq four individual subunit types: NR2A, NR2B, NR2C, and NR2D. T. Ishii, et al., *J. Biol. Chem.*, 268:2836-2843 (1993), and D. J. Laurie et al., *Mol. Brain Res.*, 51:23-32 (1997) describe how the various resulting combinations produce a variety of NMDA receptors differing in physiological and pharmacological properties such as ion gating properties, magnesium sensitivity, pharmacological profile, as well as in anatomical distribution.

For example, while NR1 is found throughout the brain, NR2 subunits are differentially distributed. In particular, it is believed that the distribution map for NR2B lowers the probability of side effects while treating Parkinson's disease or pain. Thus, it would be desirable to provide novel NMDA antagonists that target the NR2B receptor.

SUMMARY OF THE INVENTION

The present invention relates to N-substituted nonarylheterocyclic compounds represented by Formula (I):

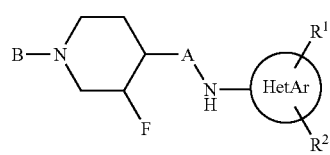

or pharmaceutically acceptable salts thereof. The present invention also provides pharmaceutical compositions comprising the instant compounds. This invention further provides methods to treat and prevent conditions, including Parkinson's disease, pain, Alzheimer's disease and epilepsy, utilizing the present compounds and compositions.

DETAILED DESCRIPTION OF THE INVENTION

The compounds of this invention are represented by Formula (I):

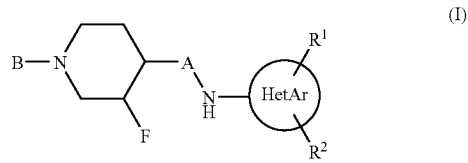

or pharmaceutically acceptable salts thereof, wherein

HetAr is a 5 or 6 membered heteroaromatic ring containing 1 or 2 nitrogen ring atoms, or thiazolyl, or thiadiazolyl;

$R^1$ and $R^2$ are independently H, $C_{1-4}$alkyl, fluoro, chloro, bromo, or iodo;

A is a bond or —$C_{1-2}$alkyl-; and

B is aryl$(CH_2)_{0-3}$—O—C(O)—, indanyl$(CH_2)_{0-3}$—C(O)—, aryl$(CH_2)_{1-3}$—C(O)—, aryl-cyclopropyl-C(O)—, aryl$(CH_2)_{1-3}$—NH—C(O)—, wherein any of the aryl is optionally substituted by 1-5 substitutents, each substituent independently is $C_{1-4}$alkyl, fluoro, or chloro.

In one aspect, the compounds of this invention are represented by Formula (I), or pharmaceutically acceptable salts thereof, wherein HetAr is a 6 membered heteroaromatic ring containing 1 or 2 nitrogen ring atoms.

In an embodiment of this first aspect, the compounds of this invention are represented by Formula (I) or pharmaceutically acceptable salts thereof, wherein HetAr is a 6 membered heteroaromatic ring containing 1 nitrogen ring atom.

In another embodiment of this first aspect, the compounds of this invention are represented by Formula (I) or pharmaceutically acceptable salts thereof, wherein HetAr is a 6 membered heteroaromatic ring containing 2 nitrogen ring atoms.

In a second aspect, the compounds of this invention are represented by Formula (I) or pharmaceutically acceptable salts thereof, wherein HetAr is thiazolyl or thiadiazolyl.

In an embodiment of this second aspect, the compounds of this invention are represented by Formula (I) or pharmaceutically acceptable salts thereof, wherein HetAr is 1,2,4-thiadiazolyl.

In another embodiment of this second aspect, the compounds of this invention are represented by Formula (I) or pharmaceutically acceptable salts thereof, wherein HetAr is thiazolyl.

In a third aspect, the compounds of this invention are represented by Formula (I) or pharmaceutically acceptable salts thereof, wherein A is a bond or —$C_{1-2}$alkyl-.

In an embodiment of this third aspect, the compounds of this invention are represented by Formula (I) or pharmaceutically acceptable salts thereof, wherein A is a bond.

In an other embodiment of this third aspect, the compounds of this invention are represented by Formula (I) or pharmaceutically acceptable salts thereof, wherein A is methylene.

In a further embodiment of this third aspect, the compounds of this invention are represented by Formula (I) or pharmaceutically acceptable salts thereof, wherein A is —$C_2$ alkyl-.

In a fourth aspect, the compounds of this invention are represented by Formula (I) or pharmaceutically acceptable salts thereof, wherein B is aryl-cyclopropyl-C(O)— or aryl($CH_2$)$_{0-3}$—O—C(O)—, wherein the aryl is optionally substituted with $C_{1-4}$alkyl.

In an embodiment of this fourth aspect, the compounds of this invention are represented by Formula (I) or pharmaceutically acceptable salts thereof, wherein B is aryl-cyclopropyl-C(O)—, wherein the aryl is phenyl, optionally substituted with $C_{1-4}$alkyl.

In another embodiment of this fourth aspect, the compounds of this invention are represented by Formula (I) or pharmaceutically acceptable salts thereof, wherein B is aryl($CH_2$)$_{0-3}$—O—C(O)—, wherein the aryl is phenyl, optionally substituted with $C_{1-4}$alkyl.

In a further embodiment of this fourth aspect, the compounds of this invention are represented by Formula (I) or pharmaceutically acceptable salts thereof, wherein B is aryl-O—C(O)—, wherein the aryl is phenyl, optionally substituted with $C_{1-4}$alkyl.

In a still further embodiment of this fourth aspect, the compounds of this invention are represented by Formula (I) or pharmaceutically acceptable salts thereof, wherein B is aryl($CH_2$)—O—C(O)—, wherein the aryl is phenyl, optionally substituted with $C_{1-4}$alkyl.

In yet another embodiment of this fourth aspect, the compounds of this invention are represented by Formula (I) or pharmaceutically acceptable salts thereof, wherein B is aryl($CH_2$)—O—C(O)—, wherein the aryl is 4-tolyl.

In a fifth aspect, the compounds of this invention are represented by Formula (I) or pharmaceutically acceptable salts thereof, wherein HetAr is a 6 membered heteroaromatic ring containing 2 nitrogen ring atoms;

A is methylene; and

B is aryl($CH_2$)—O—C(O)—, wherein the aryl is 4-tolyl.

In a sixth aspect, the compounds of this invention are represented by Formula (I) or pharmaceutically acceptable salts thereof, wherein HetAr is 1,2,4-thiadiazolyl;

A is methylene; and

B is aryl(CH2)—O—C(O)—, wherein the aryl is 4-tolyl.

In a seventh aspect, the compounds of this invention are represented by Formula (I) or pharmaceutically acceptable salts thereof, wherein HetAr is a 6 membered heteroaromatic ring containing 2 nitrogen ring atoms;

A is methylene;

B is aryl-cyclopropyl-C(O)—, wherein the aryl is phenyl, optionally substituted with $C_{1-4}$alkyl.

As used herein, "alkyl" as well as other terms having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like.

The term "aryl", unless specifically stated otherwise, includes optionally substituted multiple and single ring systems such as, for example, phenyl, naphthyl and tolyl.

The term "HetAr" includes, for example, heteroaromatic rings such as pyrimidine and pyridine.

The term "($CH_2$)$_0$" means that the methyl is not present. Thus, "($CH_2$)$_{0-3}$" means that there are from none to three methyls present—that is, three, two, one, or no methyl present. When no methyl groups are present in a linking alkyl group, the link is a direct bond.

The term "optionally substituted" is intended to include both substituted and unsubstituted. Thus, for example, optionally substituted aryl can represent a pentafluorophenyl or a phenyl ring. Further, the substitution can be made at any of the groups. For example, substituted aryl($C_{1-6}$)alkyl includes substitution on the aryl group as well as substitution on the alkyl group.

Compounds described herein may contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

The pharmaceutical compositions of the present invention comprise a compound represented by Formula I (and/or pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, and/or pharmaceutically acceptable salt(s) thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.5 mg to about 5 g of the active ingredient and each cachet or capsule preferably containing from about 0.5 mg to about 5 g of the active ingredient.

The pharmaceutical compositions of the present invention comprise a compound represented by Formula I (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The phanraceutical compositions may be conveniently presented in unit dosage form and prepared by any of the methods well known in the art of pharmacy.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrriental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the cornpound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, and/or pharmaceutically acceptable salts thereof, may also be prepared in powder or liquid concentrate form.

Assays

Cell-Based Functional Assay to Determine the $IC_{50}$ of NR2B Antagonists

The ability of selected compounds to inhibit NR1a/NR2B NMDA receptor, as measured by NR1a/NR2B receptor-mediated $Ca^{2+}$ influx, was assessed by the following calcium flux assay procedure:

NR1a/NR2B receptor transfected L(tk-) cells were plated in 96-well format at $3 \times 10^4$ cells per well and grown for one to two days in normal growth medium (Dulbeccos MEM with Na pyruvate, 4500 mg glucose, pen/strep, glutarnine, 10%

FCS and 0.5 mg/mL geneticin). NR1a/NR2B-expression in these cells was induced by the addition of 4-20 nM dexamethasone in the presence of 500 μM ketamine for 16-24 hours. Solutions of NR2B antagonists were prepared in DMSO and serially diluted with DMSO to yield 10 solutions differing by 3-fold in concentration. A 96-well drug plate was prepared by diluting the DMSO solution 250-fold into assay buffer (Hanks Balanced Salt Solution (HBSS) $Mg^{2+}$ free (Gibco #14175-079) containing 20 mM HEPES, 2 mM $CaCl_2$, 0.1% BSA and 250 μM Probenecid (Sigma # P-8761)). After induction, the cells were washed twice (Labsystem cell washer, 3 fold dilutions leaving 100 μL) with assay buffer and loaded with 4 μM of the calcium fluorescence indicator fluo-3 AM (Molecular Probes # P-1241) in assay buffer containing Pluronic F-127 (Molecular Probes # P-3000) and 10 μM ketamine at 37° C. for one hour. The cells were then washed eight times with assay buffer leaving 100 μL of buffer in each well. Fluorescence intensity was immediately measured in a FLIPR (Fluorometric Imaging Plate Reader, Molecular Devices) using an excitation of 488 nm and emission at 530 nm. Five seconds after starting the recording of fluorescence intensity, 50 μL of agonist solution (40 μM glutamate/glycine, the final concentration 10 μM) was added and after one minute, when fluorescence signal was stable, 50 μL of NR2B antagonists and control solutions from the drug plate were added and the fluorescence intensity recorded for another 30 minutes. The $IC_{50}$ values were determined by a non-linear least squares fitting of the endpoint fluorescence values to Equation #1 below.

$$\text{Endpoint Florescence} = \frac{(Ymax - Ymin)}{1 + ([\text{Drug}]/IC_{50})^{nH}} + Ymin \quad \text{Equation \#1}$$

where, YMin is average endpoint fluorescence of the control wells containing 1 μM of AMD-2 and Ymax is the average endpoint fluorescence of wells containing 0.1% DMSO in assay buffer.

Binding Assay to Determine the $K_I$ NR2B Antagonists

The radioligand binding assay was performed at room temperature in 96-well microtiter plates with a final assay volume of 1.0 mL in 20 mM Hepes buffer (pH 7.4) containing 150 mM NaCl. Solutions of NR2B antagonists were prepared in DMSO and serially diluted with DMSO to yield 20 μL of each of 10 solutions differing by 3-fold in concentration. Non-specific binding (NSB) was assessed using AMD-1 (10 μM final concentration), and total binding (TB) was measured by addition of DMSO (2% fmal concentration). Membranes expressing NR1a/NR2B receptors (40 pM final concentration) and tritiated AMD-2 (1 nM final concentration) were added to all wells of the microtiter plate. After 3 hours of incubation at room temperature, samples are filtered through Packard GF/B filters (presoaked in 0.05% PEI, polyethylenine Sigma P-3143) and washed 10 times with 1 mL of cold 20 mM Hepes buffer per wash. After vacuum drying of the filter plates, 40 μL of Packard Microscint-20 was added and bound radioactivity determined in a Packard TopCount. The apparent dissociation constant ($K_I$), the maximum percentage inhibition (%$I_{max}$), the minimum percentage inhibition (%$I_{min}$) and the hill slope (nH) were determined by a non-linear least squares fitting the bound radioactivity (CPM bound) to Equation #2 below.

$$CPM \text{ Bound} = \frac{(SB)(\% I_{max} - \% I_{min})/100}{(1 + ([\text{DRUG}]/(K_I(1 + [AMD-2]/K_D)))^{nH})} + NSB + (SB)(100 - \% I_{max})/100 \quad \text{Equation \#2}$$

where, $K_D$ is the apparent dissociation constant for the radioligand for the receptor as determined by a hot saturation experiment and SB is the specifically bound radioactivity determined from the difference of TB and NSB control wells.

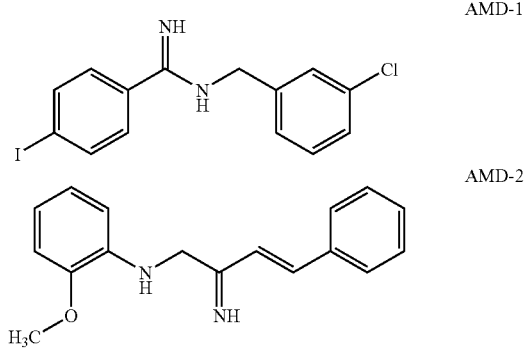

AMD-1 can be synthesized according to the general procedure described by C. F. Claiborne et al (Bioorganic & Medchem Letters 13, 697-700 (2003)

The precursor 3 for the synthesis of radiclabelled AMD-1 can be synthesized in accordance with the following procedure:

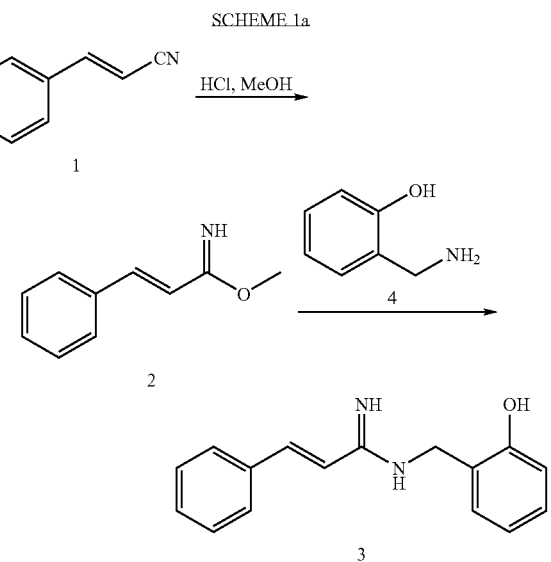

In accordance with Scheme 1a, hydrogen chloride is bubbled through a solution of cinnamonitrile 1 in methanol at room temperature. The volatiles are removed under reduced pressure and the resulting residue is triturated with ether and filtered to yield the intermediate imidate 2. Imidate 2 is dissolved in methanol at ambient temperature, treated with amine 4 (commercially available from Acros Chemicals) at ambient temperature and stirred under argon. The volatiles are removed under reduced pressure and the residue purified by preparative HPLC or trituration with ether to afford amidine 3.

Synthesis of Tritiated AMD-2

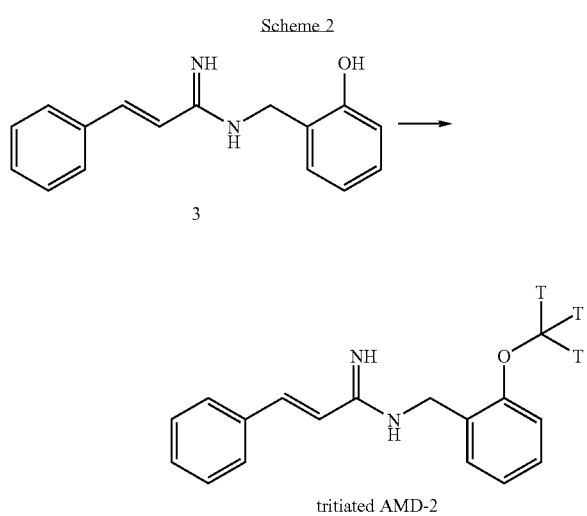

Scheme 2 tritiated AMD-2

Tritiated AMD-2 was prepared by the following procedure, illustrated in Scheme 2: The precursor 3 (2 mg, 0.008 mmol) dissolved in dimethylformamide (0.6 mL) and potassium carbonate (1.2 mg) for 1 h. High specific activity tritiated methyl iodide (50 mCi, 0.0006 mmol, in toluene 1 mL, commercially available from American Radiolabeled Chemicals) was added at room temperature and stirred for 2 hours. The reaction mixture was filtered using a Whatman PTFE 0.451 μm syringeless filter device to remove any insoluble potassium carbonate, washed with Abs. ethanol (2 mL, commercially available from Pharmco), and the combined filtrates were concentrated to dryness at room temperature using a rotary evaporator; this also removed any unreacted tritiated methyl iodide. The residue was purified by HPLC chromatography on a Phenomenx Luna C8 semi-prep column (Luna 5 micro C8(2), 250×10.0 mm) using a gradient system of 20/80 acetonitrile/water with 0.1% trifluoroacetic acid to 100% acetonitrile with 0.1% trifluoroacetic acid in 20 min. Total activity of the product was 8 mCi. Further purification was effected by absorption onto a Waters C-18 Sep-pak column (Waters Sep-Pak PLUS C18) and elution with water followed by absolute ethanol. The product was diluted with absolute ethanol (10 mL) before submission for final analysis.

Synthesis of Unlabelled AMD-2

SCHEME 1b

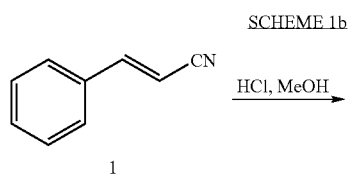

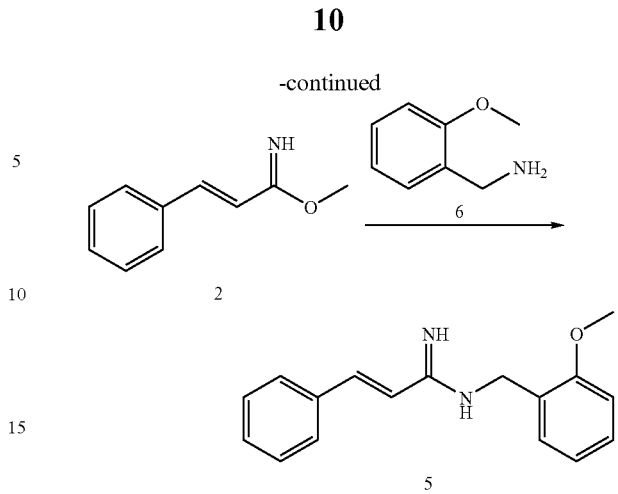

In accordance with Scheme 1b, hydrogen chloride is bubbled through a solution of cinnamonitrile 1 in methanol at room temperature. The volatiles are removed under reduced pressure and the resulting residue is triturated with ether and filtered to yield the intermediate imidate 2. Imidate 2 is dissolved in methanol at ambient temperature, treated with amine 6 at ambient temperature and stirred under argon. The volatiles are removed under reduced pressure and the residue purified by preparative HPLC or trituration with ether to afford amidine 5.

The compounds of this invention exhibit $IC_{50}$ and $K_I$ values of less than 50 μM in the functional and binding assays, respectively. It is advantageous that the $IC_{50}$ and $K_I$ values be less than 5 μM in the functional and binding assays, respectively. It is more advantageous that the $IC_{50}$ and $K_I$ values be less than 1 μM in the functional and binding assays, respectively. It is still more advantageous that the $IC_{50}$ and $K_I$ values be less than 0.1 μM in the functional and binding assays, respectively.

The present compounds are NMDA NR2B receptor antagonists, and as such are useful for the treatment and prophylaxis of diseases and disorders mediated through the NR2B receptor. Such diseases and disorders include, but are not limited to, Parkinson's disease, neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy), central pain syndromes (potentially caused by virtually any lesion at any level of the nervous system), and postsurgical pain syndromes (eg, postmastectomy syndrome, postthoracotomy syndrome, stump pain)), bone and joint pain (osteoarthritis), repetitive motion pain, dental pain, cancer pain, myofascial pain (muscular injury, fibromyalgia), perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, depression, anxiety, schizophrenia, stroke, traumatic brain injury, Alzheimer's disease, cerebral ischemia, amyotrophic lateral sclerosis, Huntington's disease, sensorineural hearing loss, tinnitus, glaucoma, neurological damage caused by epileptic seizures or by neurotoxin poisoning or by impairment of glucose and/or oxygen to the brain, vision loss caused by neurodegeneration of the visual pathway, Restless Leg Syndrome, multi-system atrophy, non-vascular headache, primary hyperalgesia, secondary hyperalgesia, primary allodynia, secondary allodynia, or other pain caused by central sensitization. Compounds of formula I may be used to prevent dyskinesias, particularly the side effects accompanying normal doses of L-Dopa. Furthermore, compounds of formula I may be used to decrease tolerance and/or dependence to opioid treatment of pain, and for treatment of withdrawal syndrome of e.g., alcohol, opioids, and cocaine.

It is understood that compounds of this invention can be administered at prophylactically effective dosage levels to prevent the above-recited conditions, as well as to prevent other conditions mediated through the NMDA NR2B receptor.

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: (1) non-steroidal anti-inflammatory agents; (2) COX-2 inhibitors; (3) bradykinin B1 receptor antagonists; (4) sodium channel blockers and antagonists; (5) nitric oxide synthase (NOS) inhibitors; (6) glycine site antagonists; (7) potassium channel openers; (8) AMPA/kainate receptor antagonists; (9) calcium channel antagonists; (10) GABA-A receptor modulators (e.g., a GABA-A receptor agonist); (11) matrix metalloprotease (MMP) inhibitors; (12) thrombolytic agents; (13) opioids such as morphine; (14) neutrophil inhibitory factor (NIF); (15) L-Dopa; (16) carbidopa; (17) levodopa/carbidopa; (18) dopamine agonists such as bromocriptine, pergolide, pramipexole, ropinirole; (19) anticholinergics; (20) amantadine; (21) carbidopa; (22) catechol O-methyltransferase ("COMT") inhibitors such as entacapone and tolcapone; (23) Monoamine oxidase B ("MAO-B") inhibitors; (24) opiate agonists or antagonists; (25) 5HT receptor agonists or antagonists; (26) NMDA receptor agonists or antagonists; (27) NK1 antagonists; (28) selective serotonin reuptake inhibitors ("SSRI") and/or selective serotonin and norepinephrine reuptake inhibitors ("SSNRI"); (29) tricyclic antidepressant drugs, (30) norepinephrine modulators; (31) lithium; (32) valproate; and (33) neurontin (gabapentin).

Creams, ointments, jellies, solutions, or suspensions containing the instant compounds can be employed for topical use. Mouth washes and gargles are included within the scope of topical use for the purposes of this invention.

A formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms can generally contain between from about 1 mg to about 1000 mg of the active ingredient.

The conditions recited herein can be treated or prevented by the administration of from about 0.01 mg to about 140 mg of the instant compounds per kilogram of body weight per day.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy. For example, inflammatory pain may be effectively treated by the administration of from about 0.1 mg to about 75 mg of the present compound per kilogram of body weight per day, or alternatively about 0.5 mg to about 3.5 g per patient per day. Neuropathic pain may be effectively treated by the administration of from about 0.01 mg to about 125 mg of the present compound per kilogram of body weight per day, or alternatively about 0.5 mg to about 5.5 g per patient per day.

The abbreviations used herein are as follows unless specified otherwise:

| 4-MeBnOH | 4-Methylbenzyl alcohol |
|---|---|
| CDI | 1,1'-Carbonyldiimidazole |
| TEA | Triethylamine |
| TBSCl | t-Butyldimethylsilyl chloride |
| DMF | Dimethylformamide |
| (+)-BINAP | (+)-2,2'-Bis(diphenylphosphino)-1,1'-binaphthyl |
| NaOtBu | Sodium t-butoxide |
| DIPEA | Diisopropylethylamine |
| EtOAc | Ethyl acetate |
| TBSOTf | t-Butyldimethylsilyl triflate |
| TBS | t-butyldimethylsilyl |
| THF | Tetrahydrofuran |
| DMAP | 4-Dimethylaminopyridine |
| RT | Room temperature |
| h | Hours |
| min | Minutes |
| DCM | Dichloromethane |
| MeCN | Acetonitrile |
| iPrOH | 2-Propanol |
| n-BuOH | 1-Butanol |
| EDC | 1-(3-Dimethylaminopropyl)-3-ethylcarbodiimide hydrochloride |
| HOAt | 1-Hydroxy-7-azabenzotriazole |

Methods of Synthesis

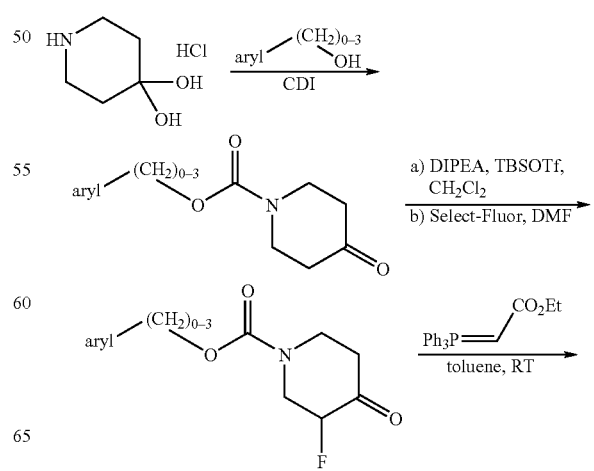

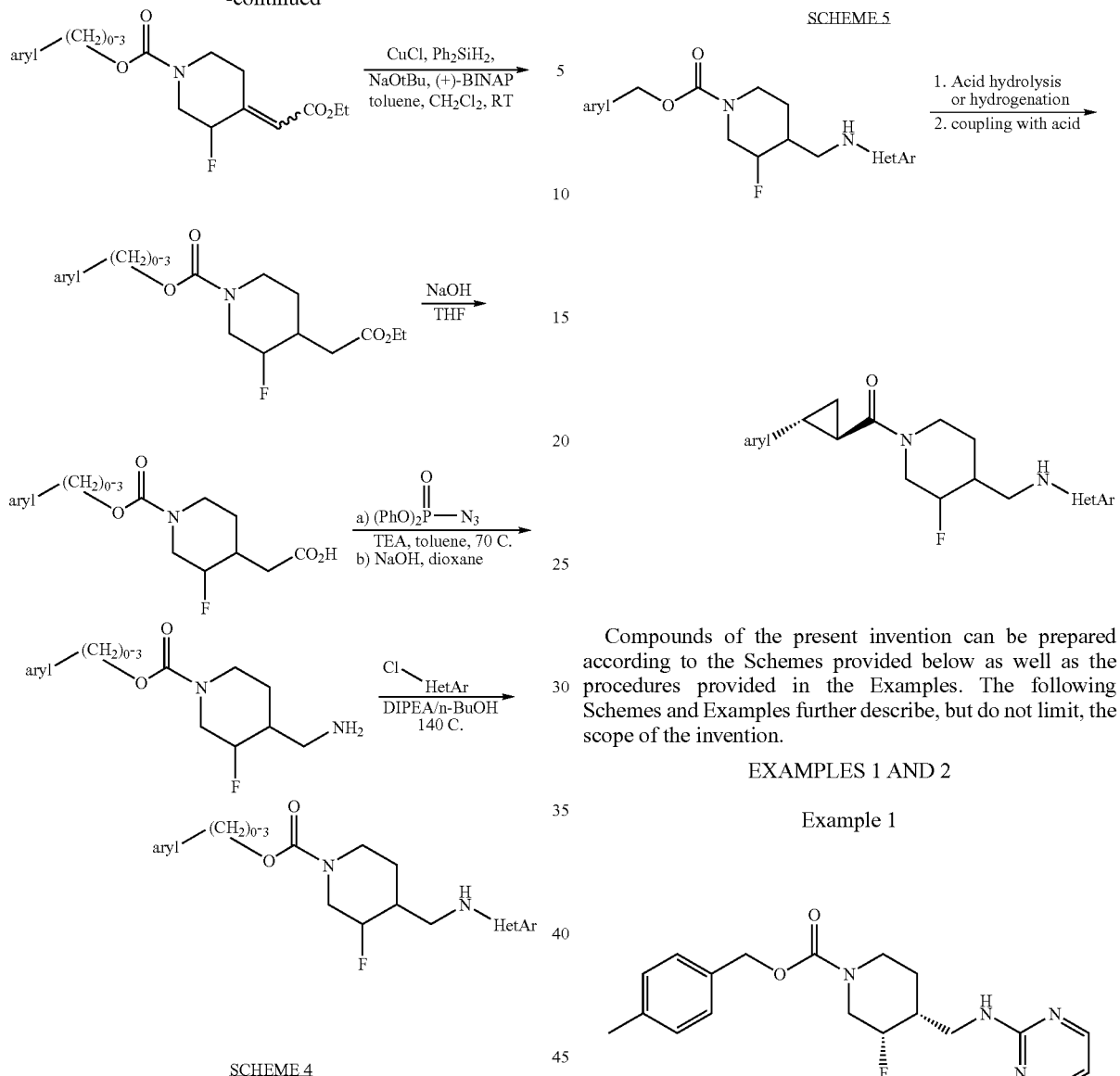
Compounds of the present invention can be prepared according to the Schemes provided below as well as the procedures provided in the Examples. The following Schemes and Examples further describe, but do not limit, the scope of the invention.
EXAMPLES 1 AND 2
Example 1
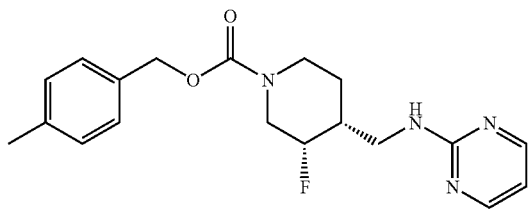
(3S,4R)-4-methylbenzyl 3-fluoro-4-[(pyrimidin-2-ylamino)methyl]piperidine-1-carboxylate
Example 2
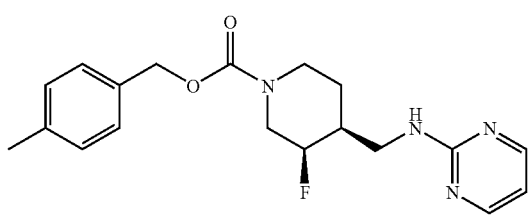

(3R,4S)-4-methylbenzyl 3-fluoro-4-[(pyrimidin-2-ylamino)Methyl]piperidine-1-carboxylate Step 1 preparation of 4-methylbenzyl 4-oxopiperidine-1-carboxylate

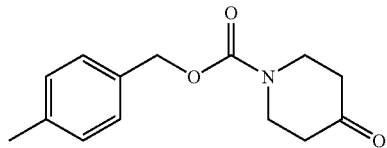

4-Methylbenzyl alcohol (37.6 g, 308 mmol) was added to a solution of 1,1'-carbonyldiimidazole (50.0 g, 308 mmol) in DMF at RT and stirred for 1 h. 4-Piperidone hydrate hydrochloride (commercially available from Sigma-Aldrich, 47.0 g, 308 mmol) was added, resulting in a reaction mixture that was then heated to 50° C. and stirred for 15 h. The reaction mixture was diluted with EtOAc and washed with 0.1 M HCl, $H_2O$ (four times), and brine, dried over $Na_2SO_4$, filtered and concentrated. Purification by silica gel chromatography (step gradient elution: 10%, 25%, 50% EtOAc in hexanes) produced the title compound (42.4 g, 85% yield) as a clear oil.

$^1$H NMR (400 MHz, $CDCl_3$) δ 7.24 (d, 2 H), 7.15 (d, 2 H), 5.08 (s, 2 H), 3.79 (t, 4 H), 2.45 (br s, 4 H) 2.31 (s, 3 H) ppm;

HRMS (ES) m/z 248.1281 [(M+H)$^+$; calcd for $C_{14}H_{18}NO_3$: 248.1287]; Anal. $C_{14}H_{17}NO_3$: C, 68.03; H, 7.05; N, 5.59. Found: C, 68.00; H, 6.93; N, 5.66.

Step 2

Preparation of (±)-4-methylbenzyl 3-fluoro-4-oxopiperidine-1-carboxylate

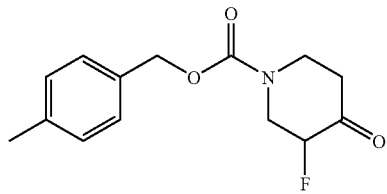

A solution of 4-methylbenzyl 4-oxopiperidine-1-carboxylate (21.2 g, 85.7 mmol) and diisopropylethylamine (71.3 mL, 428 mmol) in dichloromethane (425 mL) was cooled to 0° C. and stirred. TBSOTf (29.5 mL, 129 mmol) was added slowly, maintaining the internal temperature below 5° C. Aqueous $NaHCO_3$ (20 mL) was added and the layers were separated. The organic layer was washed with $NaHCO_3$, $H_2O$ (two times), and brine, dried over $Na_2SO_4$, filtered and concentrated to give the crude TBS enol ether.

The crude TBS enol ether was dissolved in DMF (125 mL) at RT. Selectfluor® reagent (commercially available from Air Products and Chemicals, Inc., 30.4 g, 85.7 mmol) was added and the reaction mixture was stirred for 10 min. The reaction mixture was partitioned between EtOAc and $H_2O$ and the organic layer was washed with $H_2O$ (three times). The combined aqueous layers were extracted with EtOAc (two times) and the combined organics were dried over $Na_2SO_4$, filtered and concentrated. The entire reaction above was repeated and the resulting reaction products were combined to give the title compound (40 g), which was used in the next step without purification. NMR and mass spectral data suggest the ketone functionality in the product exists as a hydrate.

$^1$H NMR (400 MHz, $CDCl_3$) δ 7.24 (m, 2 H), 7.19 (m, 2 H), 5.18 (s, 2 H), 4.81 (br d, 1 H), 4.50 (br d, 1H), 4.23 (d, 1 H), 3.90 (m, 1 H), 3.60 (m, 1 H), 3.35 (t, 1 H), 2.58 (m, 2 H), 2.35 (s, 3 H) ppm;

HRMS (ES) m/z 284.1292 [(M+H)$^+$; calcd for $C_{14}H_{18}FNO_4$: 284.1293]; Anal. $C_{14}H_{18}FNO_4 \cdot 1.2\ H_2O$: C, 58.61; H, 6.46; N, 4.88. Found: C, 58.28; H, 6.06; N, 4.72.

Step 3

Preparation of:

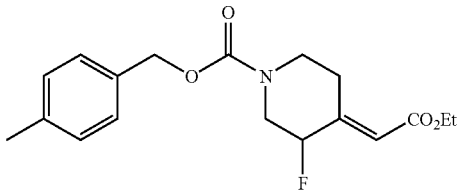

(±)-4-methylbenzyl (E)-4-(2-ethoxy-2-oxoethylidene)-3-fluoropiperidine-1-carboxylate and

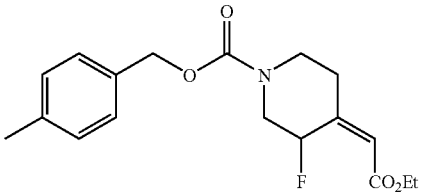

(±)-4-methylbenzyl (Z)-4-(2-ethoxy-2-oxoethylidene)-3-fluoropiperidine-1-carboxylate To a solution of (±)-4-methylbenzyl 3-fluoro-4-oxopiperidine-1-carboxylate (40 g, 150 mmol) in toluene (200 mL) at RT was added (carbethoxymethylene)triphenylphosphorane (63.0 g, 181 mmol) and the reaction mixture stirred for 1 h. The reaction mnixture was concentrated and purified by silica gel chromatography (gradient elution: 10% to 20% EtOAc in hexanes) to give the olefins (±)-4-methylbenzyl (E)-4-(2-ethoxy-2-oxoethylidene)-3-fluoropiperidine-1-carboxylate and (±)-4-methylbenzyl (Z)-4-(2-ethoxy-2-oxoethylidene)-3-fluoropiperidine-1-carboxylate (41.0 g, 78% yield, 3 steps) as a 3:1 E:Z mixture. This mixture was utilized directly in the next step. A small sample of the mixture was separated by silica gel chromatography for characterization purposes.

(±)-4-Methylbenzyl (E)-4-(2-Ethoxy-2-Oxoethylidene)-3-Fluoropiperidine-1-Carboxylate: white solid $^1$H NMR (400 MHz, $CDCl_3$) δ 7.26 (d, 2 H), 7.17 (d, 2 H), 5.98 (s, 1 H), 5.11 (s, 2 H), 4.85 (m, 1 H), 4.18 (q, 2 H), 4.08

(br d, 1 H), 3.70 (m, 1 H), 3.55 (m, 1 H) 3.41 (m, 1 H), 3.33, (m, 1 H), 2.63 (br d, 1H), 2.35 (s, 3 H), 1.29 (t, 3 H) ppm;

HRMS (ES) m/z 358.1420 [(M+Na)+; calcd for $C_{18}H_{22}FNO_4Na$: 358.1425]; Anal. $C_{18}H_{22}FNO_4$: C, 64.21; H, 6.58; N, 4.27. Found: C, 64.46; H, 6.61; N, 4.18.

(±)-4-methylbenzyl (Z)-4-(2-ethoxy-2-oxoethylidene)-3-fluoropiperidine-1-carboxylate: white solid $^1$H NMR (400 MHz, $CDCl_3$) δ 7.24 (d, 2 H), 7.15 (d, 2 H), 6.41 (m, 1 H), 5.82 (s, 1 H), 5.11 (d, 2 H), 4.61 (m, 1 H), 4.38 (br d, 1 H), 4.16 (q, 2 H), 3.05-2.95 (m, 1 H), 2.9-2.75 (m, 2 H), 2.33 (s, 3 H), 2.13 (m, 1H), 1.27 (t,3 H) ppm;

HRMS (ES) m/z 358.1422 [(M+Na)+; calcd for $C_{18}H_{22}FNO_4Na$: 358.1425].

Step 4:

Preparation of:

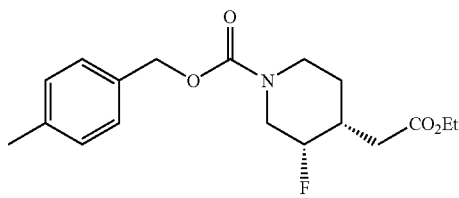

(±)-cis 4-methylbenzyl 4-(2-ethoxy-2-oxoethyl)-3-fluoropiperidine-1-carboxylate and

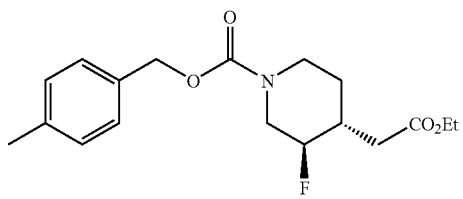

(±)-trans 4-methylbenzyl 4-(2-ethoxy-2-oxoethyl)-3-fluoropiperidine-1-carboxylate To a solution of the olefin mixture from Step 3 (10.0 g, 29.8 mmol) in toluene (160 mL) and $CH_2Cl_2$ (120 mL) was added diphenylsilane (5.53 mL, 29.8 mmol) and (R)-BINAP (1.86 g, 2.98 mmol). Sodium t-butoxide (0.29 g, 2.98 mmol) and CuCl (0.30 g, 2.98 mmol) were then added, the reaction mixture was protected from light and stirred for 15 h. Additional portions of diphenylsilane (2.76 mL), NaOtBu (0.29 g) and CuCl (0.30 g) were added and the reaction mixture was stirred at RT for 24 h. The mixture was then filtered through celite and concentrated. Purification on silica gel (step gradient elution: 5%, 10%, 15%, 25%, 30% EtOAc in hexanes) gave recovered starting materials (3.5 g, 35% yield), (±)-cis 4-methylbenzyl 4-(2-ethoxy-2-oxoethyl)-3-fluoropiperidine-1-carboxylate (5.0 g, 50% yield) and (±)-trans 4-methylbenzyl 4-2-ethoxy-2-oxoethyl)-3-fluoropiperidine-1-carboxylate (1.2 g, 12% yield).

(±)-cis 4-methylbenzyl 4-(2-ethoxy-2-oxoethyl)-3-fluoropiperidine-1-carboxylate: clear oil $^1$H NMR (400 MHz, $CDCl_3$) δ 7.25 (d, 2 H), 7.15 (d, 2 H), 5.10 (s, 2 H), 4.80-4.20 (m, 3 H), 4.15 (q, 2H), 3.10-2.73 (m, 2 H), 2.52 (dd, 1 H), 2.35 (s, 3 H), 2.30 (dd, 1 H), 2.10 (m, 1 H), 1.72-1.48 (m ,2 H), 1.29 (t, 3 H) ppm;

HRMS (ES) m/z 338.1689 [(M+H)+; calcd for $C_{18}H_{25}FNO_4$: 338.1762].

(±)-trans 4-methylbenzyl 4-(2-ethoxy-2-oxoethyl)-3-fluoropiperidine-1-carboxylate: clear oil $^1$H NMR (400 MHz, $CDCl_3$) δ 7.24 (d, 2 H), 7.15 (d, 2 H), 5.08 (s, 2 H), 4.50-3.95 (m, 3 H), 4.15 (q, 2H), 2.81 (br t, 2 H), 2.70 (br d, 1 H), 2.35 (s, 3 H), 2.17 (m, 2 H), 1.89 (br d, 1 H), 1.25 (m, 1 H), 1.22 (t, 3 H) ppm;

HRMS (ES) m/z 338.1699 [(M+H)+; calcd for $C_{18}H_{25}FNO_4$: 338.1762].

Step 5

Preparation of (±)-((cis)-3-fluoro-1-{[(4-methylbenzyl)oxy]carbonyl}piperidin-4-yl)acetic acid

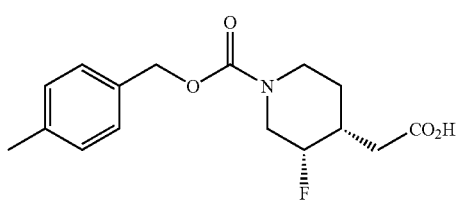

To a solution of (±)-cis 4-methylbenzyl 4-2-ethoxy-2-oxoethyl)-3-fluoropiperidine-1-carboxylate (10.0 g, 29.6 mmol) in THF (50 mL) was added aqueous NaOH (1M, 50 mL). The reaction mixture was stirred at RT for 5 h and then diluted with EtOAc and 1M HCl. The layers were separated and the aqueous extracted with EtOAc twice. The combined organics were washed with brine, dried over $Na_2SO_4$, filtered and concentrated to give the title compound (9.1 g) as a white solid which was used in the next step without further purification.

$^1$H NMR (400 MHz, $CDCl_3$) δ 7.24 (d, 2 H), 7.15 (d, 2 H), 5.08 (s, 2 H), 4.79-4.16 (m, 3 H), 3.05-2.75 (m, 2 H), 2.59 (dd, 1 H), 2.36 (dd, 1 H), 2.31 (s, 3 H), 2.20-2.02 (m, 1 H), 1.60 (m, 2 H) ppm;

HRMS (ES) m/z 310.1457 [(M+H)+; calcd for $C_{16}H_{21}FNO_4$: 310.1449]. Anal. $C_{16}H_{20}FNO_4 \cdot 0.15\ H_2O$: C, 62.13; H. 6.52; N, 4.53. Found: C, 61.55; H, 6.37; N, 4.41.

Step 6

Preparation of (±)-cis-4-methylbenzyl 4(aminomethyl)-3-fluoropiperidine-1-carboxylate

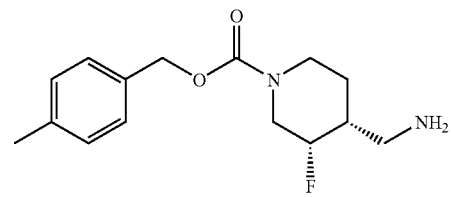

To a suspension of crude acid (±)-((cis)-3-fluoro-1-{[(4-methylbenzyl)oxy]carbonyl}piperidin-4-yl)acetic acid (9.1 g, 29.4 mmol) in toluene (80 mL) was added triethylamine (10.2 mL, 73.5 mmol) and diphenylphosphoryl azide (9.52 mL, 44.1 mmol). The reaction mixture was heated to 70° C. and stirred for 20 min. A mixture of dioxane (80 mL) and 1 M NaOH (80 mL) was added and the reaction mixture was cooled to RT. The reaction mixture was concentrated to remove the dioxane and extracted with EtOAc three times, dried over $Na_2SO_4$, filtered and concentrated. The residue was suspended in $CH_2Cl_2$, stirred for 30 min, and the white precipitate filtered off. The filtrate was concentrated to give crude product (7.5 g) as a yellow oil, used directly in the next step. An analytical sample was purified by silica gel chromatography (gradient elution: $CH_2Cl_2$ to 80:20:2 $CH_2Cl_2$:MeOH:$NH_4OH$) for characterization:

$^1$HNMR (400 MHz, $CDCl_3$) δ 7.24 (d, 2 H), 7.15 (d, 2 H), 5.08 (s, 2 H), 4.90-4.18 (m, 3 H), 2.95-2.75 (m, 2 H), 2.79 (dd, 1 H), 2.70 (dd, 1 H), 2.35 (s, 3 H), 1.59 (m, 3 H) ppm;

HRMS (ES) m/z 281.1658 [(M+H)$^+$; calcd for $C_{15}H_{22}FN_2O_2$: 281.1660].

Step 7

Preparation of:

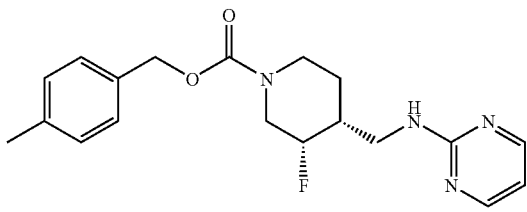

(3S,4R)-4-methylbenzyl 3-fluoro-4-[(pyrimidin-2-ylamino)methyl]piperidine-1-carboxylate and

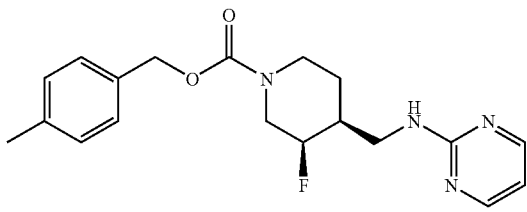

(3R,4S)-4-methylbenzyl 3-fluoro-4-[(pyrimidin-2-ylamino)methyl]piperdine-1-carboxylate Two sealed tubes were each charged with a mixture of crude (±)-cis-4-methylbenzyl 4-(aminomethyl)-3-fluoropiperidine-1-carboxylate (Step 6, 3.7 g, 13.2 mmol) and 2-chloropyrimidine (1.51 g, 13.2 mmol) in n-butanol/diisopropylethylamine (1:1, 13 mL). The tubes were sealed and the mixtures heated to 140° C. and stirred for 2 h. After cooling to RT, the reaction mixtures were combined and diluted with EtOAc and sat $NaHCO_3$. The layers were separated and the organic was washed with $H_2O$ and brine, dried over $Na_2SO_4$, filtered and concentrated. Purification by silica gel chromatography (gradient elution: 1:1 hexanes:EtOAc to EtOAc) gave racemic cis-4-methylbenzyl 3-fluoro-4-[(pyrimidin-2-ylamino)methyl]piperidine-1-carboxylate (6.9 g, 65% yield, 3 steps) as a white solid.

The enantiomers were separated by preparative HPLC on a ChiralPak AD column (5 cm×50 cm, 20 μM) with MeOH:MeCN (15:85, 150 mL/min) as eluant. The HCl salt of Example 1 was prepared by dissolving (3S,4R)-cismethylbenzyl 3-fluoro-4-[(pyrimidin-2-ylamino)methyl]piperidine-1-carboxylate (6.9 g, 19.3 mmol) in iPrOH (100 mL) at 65° C. A solution of HCl in iPrOH (1.608 M, 12.6 mL, 20.2 mmol) was added and the solution was slowly cooled to RT over 15 h. $Et_2O$ (25 mL) was added, the mixture stirred for 3 h, cooled to 0° C., stirred for 1 h and filtered to give (3S,4R)-4-methylbenzyl 3-fluoro-4-[(pyrimidin-2-ylamino)methyl]piperidine-1-carboxylate hydrochloride as a white solid (7.0 g, 92% recovery).

The hydrochloride salt of (3R,4S)-4-methylbenzyl-3-fluoro-4-[(pyrimidin-2-ylamino)methyl]piperidine-1-carboxylate was prepared using a similar procedure.

(3S,4R)-4-methylbenzyl 3-fluoro-4-[(pyrimidin-2-ylamino)methyl]piperidine-1-carboxylate.HCl $[α]_D$–36.4° (c 0.17, MeOH);

Melting Point 149-150° C.;

$^1$H NMR (400 MHz, $CD_3OD$) δ 8.58 (br s, 2 H), 7.21 (d, 2 H), 7.17 (d, 2 H), 6.99 (t, 1 H), 5.06 (s, 2 H), 4.79 (m, 1 H), 4.42 (t, 1 H), 4.21 (d, 1 H), 3.60 (dd, 1 H), 3.50 (dd, 1 H), 3.15-2.80 (m, 2 H), 2.30 (s, 3H),2.10 (m, 1 H), 1.61 (m, 2 H) ppm;

HRMS (ES) m/z 359.1879 [(M+H)$^+$; calcd for $C_{19}H_{24}FN_4O_2$: 359.1878]; Anal. $C_{19}H_{23}FN_4O_2$.HCl.0.2 $H_2O$: C, 57.27; H. 6.17; N, 14.06. Found: C, 57.22; H, 6.37; N, 14.16.

(3R,4S)-4-methylbenzyl 3-fluoro-4-[(pyrimidin-2-ylamino)methyl]piperidine-1-carboxylate.HCl $[α]_D$+34.90° (c 0.18, MeOH);

Melting Point 149-150° C.;

$^1$H NMR (400 MHz, $CD_3OD$) δ 8.58 (br s, 2 H), 7.21 (d, 2 H), 7.17 (d, 2 H), 6.99 (t, 1 H), 5.06 (s, 2 H), 4.79 (m, 1 H), 4.42 (t, 1 H), 4.21 (d, 1 H), 3.60 (dd, 1 H), 3.50 (dd, 1 H), 3.15-2.80 (m, 2 H), 2.30 (s, 3H), 2.10 (m, 1 H), 1.61 (m, 2 H) ppm;

HRMS (ES) m/z 359.1870 [(M+H)$^+$; calcd for $C_{19}H_{24}FN_4O_2$: 359.1878]. Anal. $C_{19}H_{23}FN_4O_2$.HCl.0.5$H_2O$: C, 56.50; H, 6.24; N, 13.87. Found: C, 56.68; H, 6.27; N, 13.80.

EXAMPLES 3 AND 4

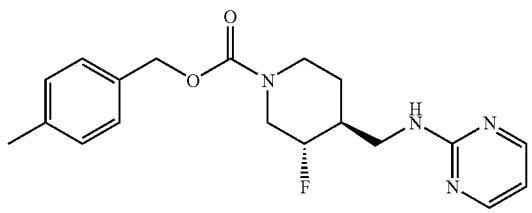

(−)-trans-4-methylbenzyl 3-fluoro-4-[(pyrimidin-2-ylamino)methyl]piperidine-1-carboxylate (Example 3) and (+)-trans-4-methylbenzyl 3-fluoro-4-[(pyrimidin-2-ylamino)methyl]piperidine-1-carboxylate (Example 4)

The title compounds were prepared from (±)-trans 4-methylbenzyl 4-(2-ethoxy-2-oxoethyl)-3-fluoropiperidine-1-carboxylate (Examples 1 and 2, Step 4), utilizing the procedures described in Steps 5, 6 and 7 from Examples 1 and 2.

(−)-trans-4-methylbenzyl 3-fluoro-4[(pyrimidin-2-ylamino)methyl]piperidine-1-carboxylate.HCl $[\alpha]_D$ −11.5° (c 0.22, MeOH);
Melting Point 113-114° C.;
$^1$H NMR (400 MHz, CD$_3$OD) δ 8.80-8.39 (m, 2 H), 7.24 (d, 2 H), 7.15 (d, 2 H), 7.00 (t, 1 H), 5.08 (s, 2H), 4.49-4.21 (m, 2 H), 4.00 (d, 1 H), 3.81 (dd, 1 H), 3.58 (dd, 1 H), 2.95 (, 1 H), 2.31 (s, 3 H), 2.12 (m, 1 H), 1.90 (m, 1 H), 1.34 (m, 1 H) ppm;
HRMS (ES) m/z 359.1867 [(M+H)$^+$; calcd for C$_{19}$H$_{24}$FN$_4$O$_2$: 359.1878]. Anal. C$_{19}$H$_{23}$FN$_4$O$_2$.HCl.H$_2$O: C, 55.27; H, 6.35; N, 13.57. Found: C, 55.08; H, 6.11; N, 13.36.

(+)-trans-4-methylbenzyl 3-fluoro-4-[(pyrimidin-2-ylamino)methyl]piperidine-1-carboxylate.HCl $[\alpha]_D$ +16.3° (c 0.17, MeOH);

Melting Point 113-114° C.

$^1$H NMR (400 MHz, CD$_3$OD) δ 8.80-8.39 (m, 2 H), 7.24 (d, 2 H), 7.15 (d, 2 H), 7.00 (t, 1 H), 5.08 (s, 2H), 4.49-4.21 (m, 2 H), 4.00 (d, 1 H), 3.81 (dd, 1 H), 3.58 (dd, 1 H), 2.95 (m, 1 H), 2.31 (s, 3 H), 2.12 (m, 1 H), 1.90 (m, 1 H), 1.34 (m, 1 H) ppm;

HRMS (ES) m/z 359.1873 [(M+H)$^+$; calcd for C$_{19}$H$_{24}$FN$_4$O$_2$: 359.1878]; Anal. C$_{19}$H$_{23}$FN$_4$O$_2$.HCl.H$_2$O: C, 55.27; H, 6.35; N, 13.57. Found: C, 55.18; H, 6.11; N, 13.38.

EXAMPLE 5

Preparation of:

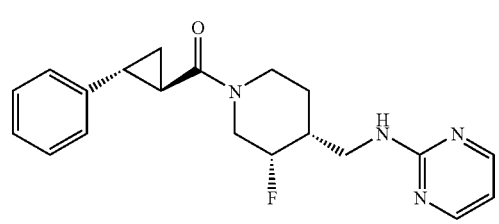

(3S,4R)-N-[(3-cis-fluoro-1-{[(1R,2R)-2-phenylcyclopropyl]carbonyl}piperidin-4-yl)methyl]pyrimidin-2-amine

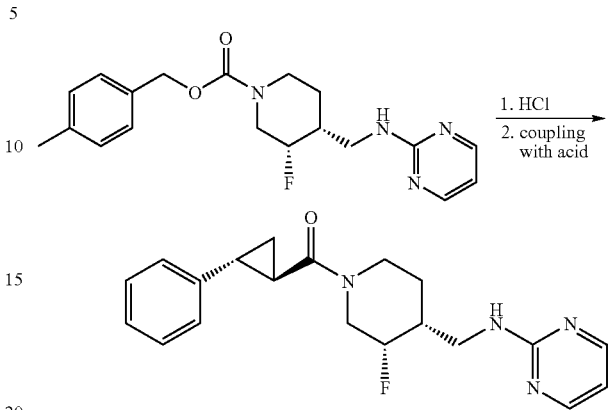

(3S,4R)-4-methylbenzyl 3-fluoro-4-[(pyrimidin-2-ylamino)methyl]piperidine-1-carboxylate (Example 1) (400 mg, 1.16 mmol) was dissolved in 3N HCl (4 mL), heated to 90° C. and stirred for 1 h. The reaction mixture was concentrated and the crude amine hydrochloride dissolved in DMF (3 mL) at RT and (1R,2R)-2-phenylcyclopropanecarboxylic acid (188 mg, 1.16 mmol) (prepared as described by T. N. Riley and C. G. Brier, J. Org. Chem, 15, 1187-1188, 1972), EDC (222 mg, 1.16 mmol); HOAt (158 mg, 1.16 mmol) and triethylamine (323 μL, 2.32 mmol) were added. The reaction mixture was heated to 70° C. and stirred for 10 min. After cooling to RT, the reaction mixture was diluted with EtOAc and H$_2$O. The layers were separated and the organic was washed with H$_2$O and brine, dried over Na$_2$SO$_4$, filtered and concentrated. Purification by silica gel chromatography (gradient elution: 1:1 hexanes:EtOAc to 90:10:1 EtOAc:MeOH:NH$_4$OH) gave the title compound (320 mg, 78% yield) as a white solid. The compound was characterized as the hydrochloride salt, which was prepared in a similar manner to that described in Example 1, Step 7.

$[\alpha]_D$ −164° (c 0.22, MeOH);
Melting Point 127-128° C.;
$^1$H NMR (400 MHz, CD$_3$OD) δ 8.59 (br s, 2 H), 7.25 (m, 2 H), 7.17 (m, 3 H), 7.01 (t, 1 H), 4.85 (m, 2H), 4.65-4.30 (m, 2 H), 3.55 (m, 2 H), 3.30 (m, 1 H), 2.80 m, 1 H), 2.39 (m, 1 H), 2.30-2.10 (m, 2 H), 1.75 (m, 1 H), 1.55 (m, 2 H), 1.33 (m, 1 H) ppm;
HRMS (ES) m/z 355.1925 [(M+H)$^+$; calcd for C$_{20}$H$_{24}$FN$_4$O: 355.1929]; Anal. C$_{20}$H$_{23}$FN$_4$O.HCl.H$_2$O: C, 58.75; H, 6.41; N, 13.70. Found: C, 58.57; H, 6.44; N, 13.54.

EXAMPLE 6

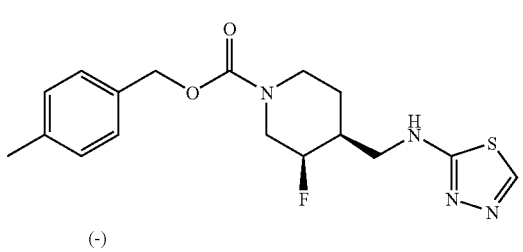

(−)

(−)-cis-4-methylbenzyl 3-fluoro-4-[(1,3,4-thiadiazol-2-ylamino)methyl]piperidine-1-carboxylate Step 1

Preparation of:

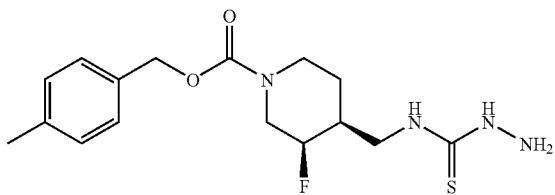

(±)-cis 4-methylbenzyl 4-{[(hydrazinocarbonothioyl)amino]methyl}-3-fluoropiperidine-1-carboxylate A solution of (±)-cis-4-methylbenzyl 4-(aminomethyl)-3-fluoropiperidine-1-carboxylate (Example 1, Step 6) (200 mg, 0.71 mmol) in DMF (2 mL) was added dropwise to a stirred and cooled (0° C.) solution of thiocarbonydiimidazole (127 mg, 0.71 mmol) in DMF (4 mL). The reaction mixture was stirred for 30 min, the cooling bath removed and the reaction mixture stirred at room temperature for 1 h. Hydrazine (0.066 mL, 2.14 mmol) was then added and the reaction mixture stirred for an additional 30 minutes. The reaction mixture was poured into water and extracted with ethyl acetate. The organic layer was washed with saturated sodium bicarbonate solution, water and brine, dried over sodium sulfate and solvent evaporated in vacuo to give crude product as a solid. The crude solid was triturated with methanol (10 mL) and filtered to give 180 mg of the title compound.

$^1$H NMR (300 MHz, CDCl$_3$) δ 7.67 (br s, 2 H), 7.25 (d, 2 H), 7.19 (d, 2 H), 5.10 (s, 2 H), 4.80-4.20 (br m, 3 H), 3.75 (s, 2 H), 3.80-3.55 (m, 2 H), 3.05-2.70 (m, 2 H), 2.38 (s, 3 H), 2.10 (m, 1 H), 1.60 (m, 2 H) ppm;

Step 2

(−)-cis-4-methylbenzyl 3-fluoro-4-[(1,3,4-thiadiazol-2-ylamino)methyl]piperidine-1-carboxylate A suspension of (±)-cis 4-methylbenzyl 4-{[(hydrazinocarbonothioyl) amino]methyl}-3-fluoropiperidine-1-carboxylate (180 mg, 0.51 mmol) in ethanol (10 mL) was treated with triethyl orthoformate (151 mg, 1.02 mmol) and concentrated HCl (0.01 mL) and stirred at room temperature, under nitrogen, for 18 h. After all solids had dissolved, the reaction mixture was heated to reflux for 1.5 hour, cooled to room temperature and the volatiles evaporated. The residue was partitioned between ethyl acetate and dilute sodium bicarbonate solution, the organic layer washed with brine, dried over sodium sulfate and solvent evaporated. The crude product was purified by gradient elution on silica gel (50% ethyl acetate: hexane to 20% methanol: ethyl acetate) to give the title compound as a white solid. The (−)-enantiomer was separated and the hydrochloride salt formed as described in Examples 1 and 2 Step 7.

[α]$_D$−47.4° (c 0.17, MeOH);
Melting Point 115-117° C.;
$^1$H NMR (400 MHz, CDCl$_3$) δ 8.37 (s, 1 H), 7.25 (d, 2 H), 7.16 (d, 2 H), 6.57 (br s, 1 H), 5.10 (d, 2 H), 4.79 (dd, 1 H), 4.56 (m, 1 H), 4.29 (m, 1 H), 3.44 (d, 2 H), 3.10-2.77 (m, 2 H), 2.35 (s, 3 H), 2.2 (m, 1 H), 1.63 (m, 2 H);

HRMS (1ES) m/z 365.1437 [(M+H)$^+$; calcd for C$_{17}$H$_{22}$FN$_4$O$_2$S: 365.1442]. Anal. C$_{17}$H$_{21}$FN$_4$O$_2$S: C, 56.03; H, 5.81; N, 15.37. Found: C, 55.82; H, 5.74; N, 15.11.

EXAMPLE 7

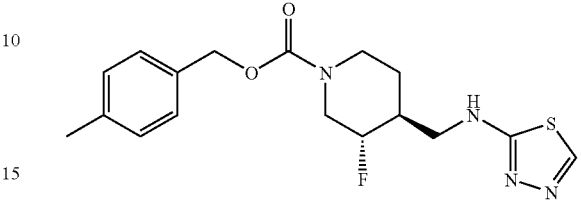

(+)-trans-4-methylbenzyl 3-fluoro-4-[(1,3,4-thiadiazol-2-ylamino)methyl]piperidine-1-carboxylate The title compound was prepared from (±)-trans 4-methylbenzyl 4-(2-ethoxy-2-oxoethyl)-3-fluoropiperidine-1-carboxylate (Examples 1 and 2, Step 4), utilizing the procedures described in Examples 1 and 2, Steps 5 and 6, followed by thiadiazole formation as described in Example 6. The (+)-enantiomer was separated by chiral HPLC as described in Example 1 and 2 Step 7.

[α]$_D$+37.1° (c 0.56, MeOH);
Melting Point 93-95° C.;
$^1$H NMR (400 MHz, CDCl$_3$) δ 8.36 (s, 1 H), 7.28 (d, 2 H), 7.19 (d, 2 H), 6.56 (br s, 1 H), 5.04 (s, 2 H), 4.45 (m, 2 H), 4.17 (m, 1 H), 3.56 (m, 2 H), 2.80 (m, 2 H), 2.35 (s, 3 H), 2.10 (m, 1 H), 1.96 (m, 1 H), 1.39 (m, 1 H) ppm;

HRMS (ES) m/z 365.1432 [(M+H)$^+$; calcd for C$_{17}$H$_{22}$FN$_4$O$_2$S: 365.1442]; Anal. C$_{17}$H$_{21}$FN$_4$O$_2$S.0.25 H$_2$O: C, 55.34; H, 5.87; N, 15.19. Found: C, 55.50; H, 5.61; N, 14.81.

What is claimed is:

1. A compound having the formula (I):

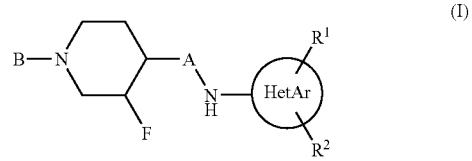

or a pharmaceutically acceptable salt thereof, wherein
HetAr is a 5 or 6 membered heteroaromatic ring containing 1 or 2 nitrogen ring atoms, thiazolyl, or thiadiazolyl, wherein the NH is linked to a carbon ortho to a nitrogen on the HetAr ring;
HetAr is optionally substituted with 1 or 2 substituents, each substituent independently is C$_{1-4}$alkyl, fluoro, chloro, bromo, or iodo;
A is a bond or —C$_{1-2}$alkyl-; and
B is aryl(CH$_2$)$_{0-3}$—O—C(O)—, indanyl(CH$_2$)$_{0-3}$—O—C(O)—, aryl(CH$_2$)$_{1-3}$—C(O)—, aryl-cyclopropyl-C(O)—, aryl(CH$_2$)$_{1-3}$—NH—C(O)—, wherein any of the aryl is optionally substituted by 1-5 substitutents, each substituent independently is C$_{1-4}$alkyl, fluoro, or chloro.

2. The compound according to claim 1, or a pharmaceutically acceptable salt thereof, wherein
HetAr is a 6 membered heteroaromatic ring containing 1 nitrogen ring atom.

3. The compound according to claim 1, or a pharmaceutically acceptable salt thereof, wherein
HetAr is a 6 membered heteroaromatic ring containing 2 nitrogen ring atoms.

4. The compound according to claim 1, or a pharmaceutically acceptable salt thereof, wherein
HetAr is thiazolyl.

5. The compound according to claim 1, or a pharmaceutically acceptable salt thereof, wherein
HetAr is thiadiazolyl.

6. The compound according to claim 1, or a pharmaceutically acceptable salt thereof, wherein
HetAr is 1,2,4 thiadiazolyl.

7. The compound according to claim 1, or a pharmaceutically acceptable salt thereof, wherein
A is a bond.

8. The compound according to claim 1, or a pharmaceutically acceptable salt thereof, wherein
A is methylene.

9. The compound according to claim 1, or a pharmaceutically acceptable salt thereof, wherein A is —C$_2$ alkyl-.

10. The compound according to claim 1, or a pharmaceutically acceptable salt thereof, wherein
B is aryl-cyclopropyl-C(O)—, wherein said aryl is optionally substituted as defined in claim 1.

11. The compound according to claim 10, or a pharmaceutically acceptable salt thereof, wherein said aryl is phenyl, optionally substituted as defined in claim 1.

12. The compound according to claim 1, or a pharmaceutically acceptable salt thereof, wherein
B is aryl(CH$_2$)$_{0-3}$—O—C(O)—, wherein said aryl is optionally substituted as defined in claim 1.

13. The compound according to claim 1, or a pharmaceutically acceptable salts thereof, wherein
B is aryl(CH$_2$)—O—C(O)—, wherein said aryl is optionally substituted as defined in claim 1.

14. The compound according to claim 13, or a pharmaceutically acceptable salt thereof, wherein said aryl is optionally substituted with C$_{1-4}$ alkyl.

15. The compound according to claim 14, or a pharmaceutically acceptable salt thereof, wherein said aryl is 4-tolyl.

16. The compound according to claim 1, or a pharmaceutically acceptable salt thereof, wherein
HetAr is a 6 membered heteroaromatic ring containing 2 nitrogen ring atoms;
A is methylene; and
B is aryl(CH$_2$)—O—C(O)—, wherein said aryl is optionally substituted as defined in claim 1.

17. The compound according to claim 16, or a pharmaceutically acceptable salt thereof, wherein
said aryl is optionally substituted with C$_{1-4}$ alkyl.

18. The compound according to claim 17, or a pharmaceutically acceptable salt thereof, wherein
said aryl is 4-tolyl.

19. The compound according to claim 1, or a pharmaceutically acceptable salt thereof, wherein
HetAr is a 6 membered heteroaromatic ring containing 2 nitrogen ring atoms;
A is methylene; and
B is 4-tolyl(CH$_2$)—O—C(O)—.

20. The compound according to claim 1, or a pharmaceutically acceptable salt thereof, wherein
HetAr is thiadiazolyl;
A is methylene; and
B is aryl(CH$_2$)—O—C(O)—, wherein said aryl is optionally substituted as defined in claim 1.

21. The compound according to claim 1, or pharmaceutically acceptable salts thereof, wherein
HetAr is 1,2,4-thiadiazolyl;
A is methylene; and
B is 4-tolyl(CH$_2$)—O—C(O)—.

22. The compound according to claim 1, or a pharmaceutically acceptable salt thereof, wherein
HetAr is a 6 membered heteroaromatic ring containing 2 nitrogen ring atoms;
A is methylene; and
B is aryl-cyclopropyl-C(O)—.

23. The compound according to claim 1, or pharmaceutically acceptable salts thereof, wherein
HetAr is a 6 membered heteroaromatic ring containing 2 nitrogen ring atoms; and
B is phenyl-cyclopropyl-C(O)—.

24. The compound according to claim 1, wherein said compound is

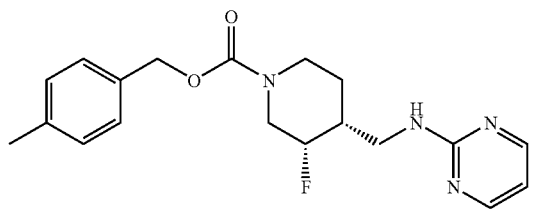

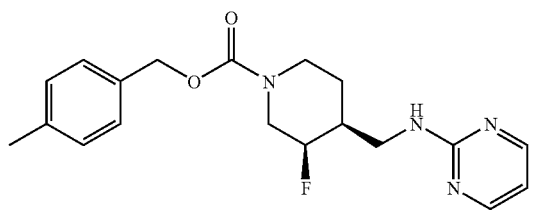

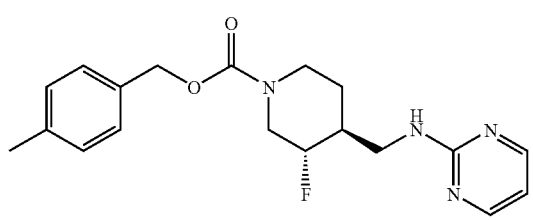

(-)

-continued

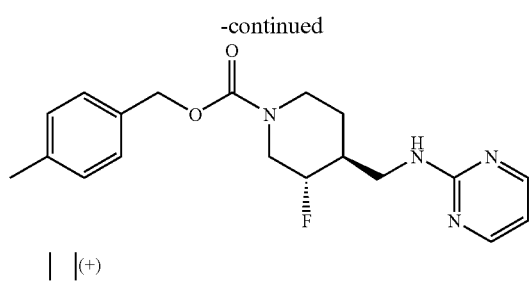

|(+)

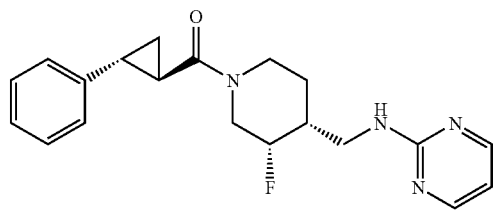

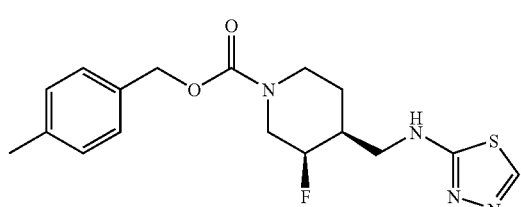
(-)

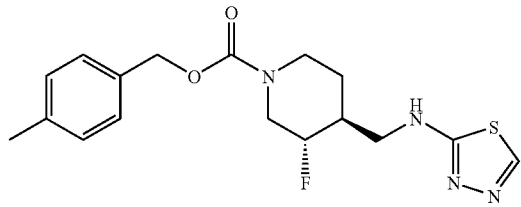
(+)

or a pharmaceutically acceptable salt thereof.

25. The compound according to claim 1, wherein said compound is

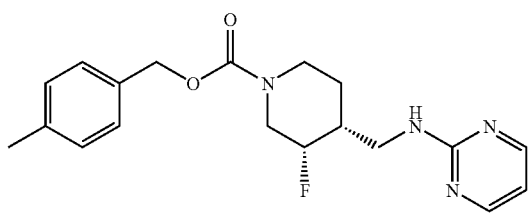

or a pharmaceutically acceptable salt thereof.

26. The compound according to claim 1, wherein said compound is

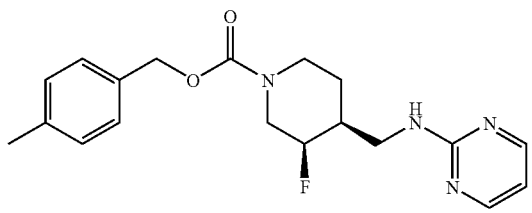

or a pharmaceutically acceptable salt thereof.

27. The compound according to claim 1, wherein said compound is

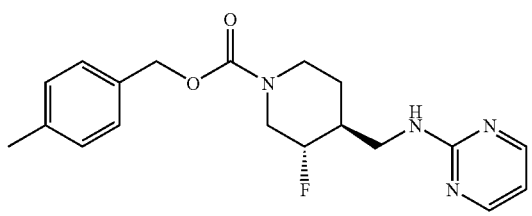
(-)

or a pharmaceutically acceptable salt thereof.

28. The compound according to claim 1, wherein said compound is

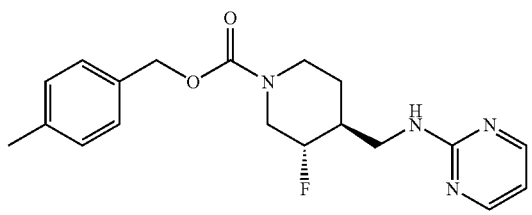
(+)

or a pharmaceutically acceptable salt thereof.

29. The compound according to claim 1, wherein said compound is

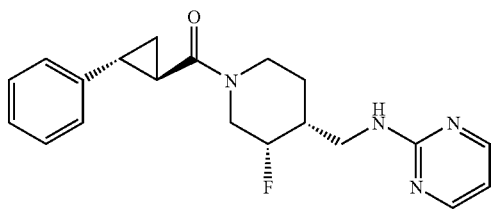

or a pharmaceutically acceptable salt thereof.

30. The compound according to claim 1, wherein said compound is

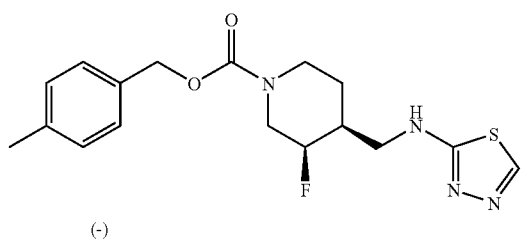

(-)

or a pharmaceutically acceptable salt thereof.

31. The compound according to claim 1, wherein said compound is

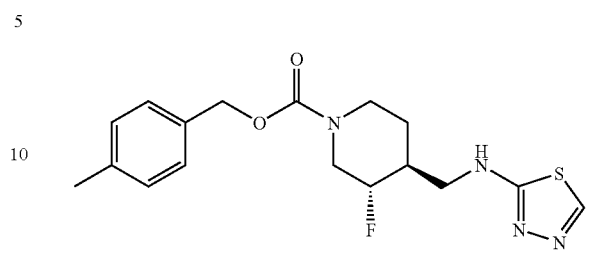

(+)

or a pharmaceutically acceptable salt thereof.

32. A pharmaceutical composition comprising an inert carrier and a therapeutically effective amount of a compound according to claim 1.

* * * * *

UNITED STATES PATENT AND TRADEMARK OFFICE
CERTIFICATE OF CORRECTION

PATENT NO. : 7,592,360 B2　　　　　　　　　　　　　　　　　　　　　　Page 1 of 1
APPLICATION NO. : 10/559153
DATED : September 22, 2009
INVENTOR(S) : Liverton et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 825 days.

Signed and Sealed this

Twenty-first Day of September, 2010

David J. Kappos
*Director of the United States Patent and Trademark Office*